(12) United States Patent
Mastrangelo

(10) Patent No.: US 10,342,287 B1
(45) Date of Patent: Jul. 9, 2019

(54) CORRECTIVE FOOTWEAR FOR LEG LENGTH DISCREPANCY

(71) Applicant: Hot Shots Ventures, LLC, Aguanga, CA (US)

(72) Inventor: Don Mastrangelo, Aguanga, CA (US)

(73) Assignee: Hot Shots Ventures, LLC, Aguanga, CA (US)

( * ) Notice: Subject to any disclaimer, the term of this patent is extended or adjusted under 35 U.S.C. 154(b) by 0 days.

(21) Appl. No.: 16/242,481

(22) Filed: Jan. 8, 2019

(51) Int. Cl.
| | | |
|---|---|---|
| *A43B 7/38* | (2006.01) | |
| *A43B 7/14* | (2006.01) | |
| *A43D 8/00* | (2006.01) | |
| *A43B 7/16* | (2006.01) | |
| *A43B 7/22* | (2006.01) | |

(52) U.S. Cl.
CPC .............. *A43B 7/144* (2013.01); *A43B 7/147* (2013.01); *A43B 7/1455* (2013.01); *A43B 7/38* (2013.01); *A43B 7/1425* (2013.01); *A43B 7/16* (2013.01); *A43B 7/223* (2013.01); *A43D 8/00* (2013.01)

(58) Field of Classification Search
CPC ................... A43B 7/147; A43B 7/38
See application file for complete search history.

(56) References Cited

U.S. PATENT DOCUMENTS

| | | | | |
|---|---|---|---|---|
| 5,177,883 A * | 1/1993 | Darby | ...... | A43B 3/26 36/103 |
| 5,714,098 A * | 2/1998 | Potter | ...... | A43B 3/26 264/40.1 |
| 8,595,081 B2 | 11/2013 | Dean et al. | | |
| 2005/0071242 A1* | 3/2005 | Allen | ...... | G06Q 10/087 705/26.5 |
| 2008/0010867 A1* | 1/2008 | Davis, III | ...... | A43B 3/0078 36/136 |
| 2009/0019648 A1* | 1/2009 | Jones | ...... | A43B 1/0027 12/146 R |
| 2011/0232008 A1* | 9/2011 | Crisp | ...... | A43B 9/00 12/18.1 |
| 2014/0215861 A1* | 8/2014 | Burks | ...... | A43B 7/38 36/30 R |
| 2015/0196086 A1* | 7/2015 | Riddle | ...... | A43B 7/142 36/25 R |
| 2015/0223558 A1* | 8/2015 | Qureshi-Pierce | ...... | A43B 7/16 36/81 |
| 2017/0245585 A1* | 8/2017 | Cook | ...... | A43B 3/126 |
| 2017/0245586 A1* | 8/2017 | Cook | ...... | A43B 13/12 |
| 2018/0157228 A1 | 6/2018 | Spector | | |

* cited by examiner

*Primary Examiner* — Ted Kavanaugh
(74) *Attorney, Agent, or Firm* — Kolitch Romano LLP

(57) ABSTRACT

Methods for providing footwear configured to treat leg length discrepancy include manufacturing a plurality of footwear members. Each footwear member has a sole thickness, with sole thicknesses of the plurality of footwear members spanning a predetermined range of thicknesses. A corrective pair of footwear may be formed by selecting a left member having a first sole thickness and a right member having a second sole thickness, wherein the difference between the first and second sole thicknesses corresponds to an amount of leg length discrepancy to be corrected.

9 Claims, 6 Drawing Sheets

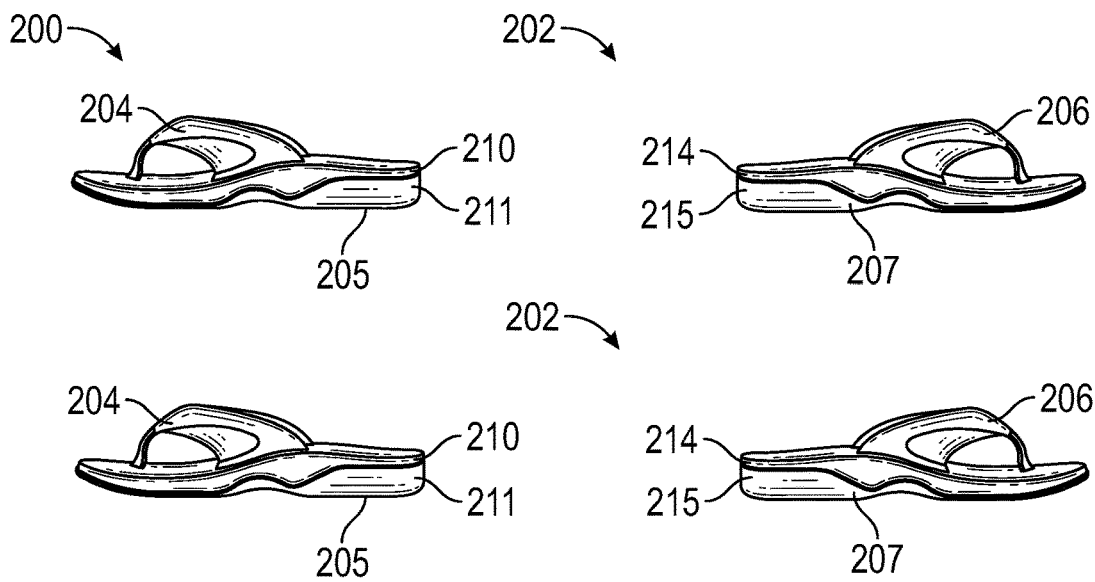
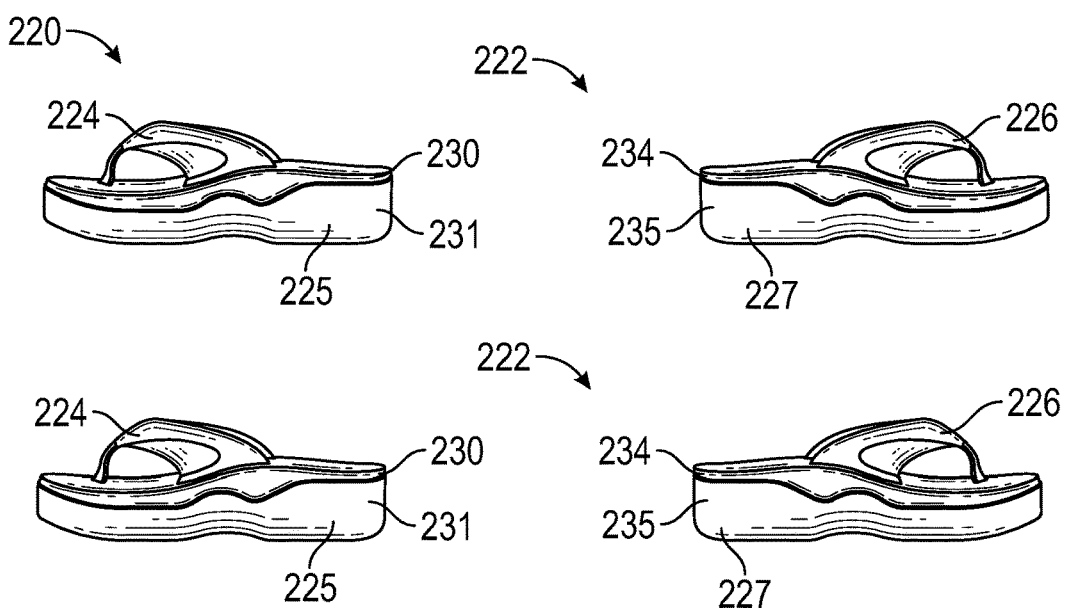
FIG. 3
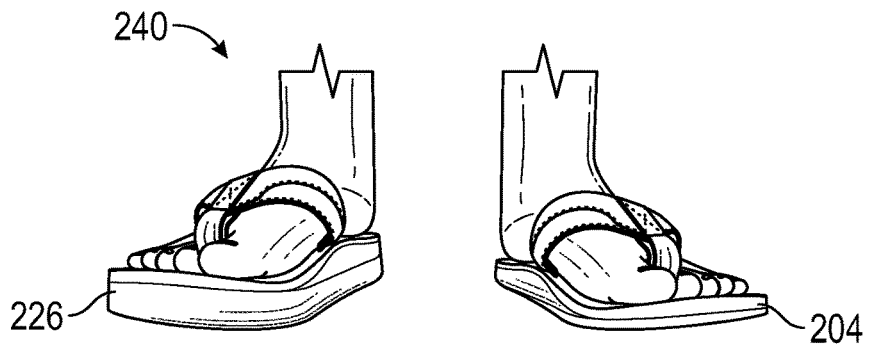
FIG. 4
FIG. 5

US 10,342,287 B1

CORRECTIVE FOOTWEAR FOR LEG LENGTH DISCREPANCY

FIELD

This disclosure relates to footwear. More specifically, the disclosed embodiments relate to systems and methods for providing footwear configured to correct leg length discrepancy.

INTRODUCTION

Leg length discrepancy (LLD), also known as leg length inequality or anisomelia, is a physical condition wherein a person's legs are unequal in length. Leg length discrepancy can result from structural differences and/or functional differences between the legs. LLD can develop later in life, for example as a side effect of knee replacement and/or hip replacement surgery on one side of the body. Most individuals have at least some amount of LLD. In many cases, the amount of LLD is too small to cause a problem or even to be noticed at all. However, a non-negligible amount of LLD can adversely affect a person's posture and gait, and may lead to health problems such as back pain, hip pain, and an increased risk of stress fractures.

According to known methods, LLD may be treated and/or compensated for by placing a shoe lift inside the shoe worn on the shorter leg. However, because such a lift is disposed substantially between the insole and the wearer's foot, the foot is displaced from its intended position within the shoe. Accordingly, the wearer may experience discomfort and reduced ankle support. Furthermore, shoes that are open at the toes or at other portions of the shoe upper are typically unable to accommodate shoe lifts, are therefore difficult for sufferers of LLD to wear and may lead to pain or injury if worn. Alternatives to lifts, such as custom-made or custom-modified shoes, typically involve deconstructing factory-made shoes and then modifying them with lifts of some type. These solutions are typically very expensive and relatively slow to obtain. A better solution is needed for providing footwear to treat LLD.

SUMMARY

The present disclosure provides systems, apparatuses, and methods relating to footwear for correcting LLD. In some embodiments, a method of providing open-toed sandals to correct leg length discrepancy comprises obtaining a first plurality of pairs of sandals, each pair of the first plurality consisting of a left member and a right member having an identical first sole thickness; obtaining a second plurality of pairs of sandals, each pair of the second plurality consisting of a left member and a right member having an identical second sole thickness which differs from the first sole thickness by at least 3 millimeters; receiving an indication of a nonzero amount of leg length discrepancy to be corrected; and providing one of the left members from the first plurality and one of the right members from the second plurality; wherein a difference between the first sole thickness and the second sole thickness corresponds to the amount of leg length discrepancy to be corrected.

In some embodiments, a method of treating leg length discrepancy without the use of an insertable footwear lift comprises manufacturing or having manufactured a plurality of pairs of footwear, wherein each pair of footwear consists of a left member and a right member having identical sole thicknesses, and wherein the plurality of pairs includes pairs with sole thicknesses spanning a predetermined range of thicknesses; receiving an indication of a nonzero amount of leg length discrepancy suffered by a person; providing one of the left members having a first sole thickness within the predetermined range; and providing one of the right members having a second sole thickness within the predetermined range; wherein the first sole thickness differs from the second sole thickness by the amount of leg length discrepancy suffered by the person.

In some embodiments, a method of providing footwear to correct leg length discrepancy comprises manufacturing or having manufactured a first plurality of pairs of footwear, each pair of the first plurality consisting of a left member and a right member, wherein all the left members and all the right members of the first plurality share an identical first sole thickness; manufacturing or having manufactured a second plurality of pairs of footwear, each pair of the second plurality consisting of a left member and a right member, wherein all the left members and all the right members of the second plurality share an identical second sole thickness which differs from the first sole thickness by at least 3 millimeters; receiving an order for corrective footwear including an indication of a nonzero amount of leg length discrepancy to be corrected; selecting one of the left members from the first plurality and one of the right members from the second plurality to form a corrective pair of footwear, wherein the first sole thickness differs from the second sole thickness by the amount of leg length discrepancy to be corrected; and providing the corrective pair of footwear in response to the order.

Features, functions, and advantages may be achieved independently in various embodiments of the present disclosure, or may be combined in yet other embodiments, further details of which can be seen with reference to the following description and drawings.

BRIEF DESCRIPTION OF THE DRAWINGS

FIG. 3 is a side view of a plurality of footwear including left and right members having a first sole thickness, in accordance with aspects of the present teachings.

FIG. 4 is a side view of another plurality of footwear including left and right members having a second sole thickness, in accordance with aspects of the present teachings.

FIG. 5 is a front view of another pair of corrective footwear, in accordance with aspects of the present teachings.

DETAILED DESCRIPTION

Figure 1:
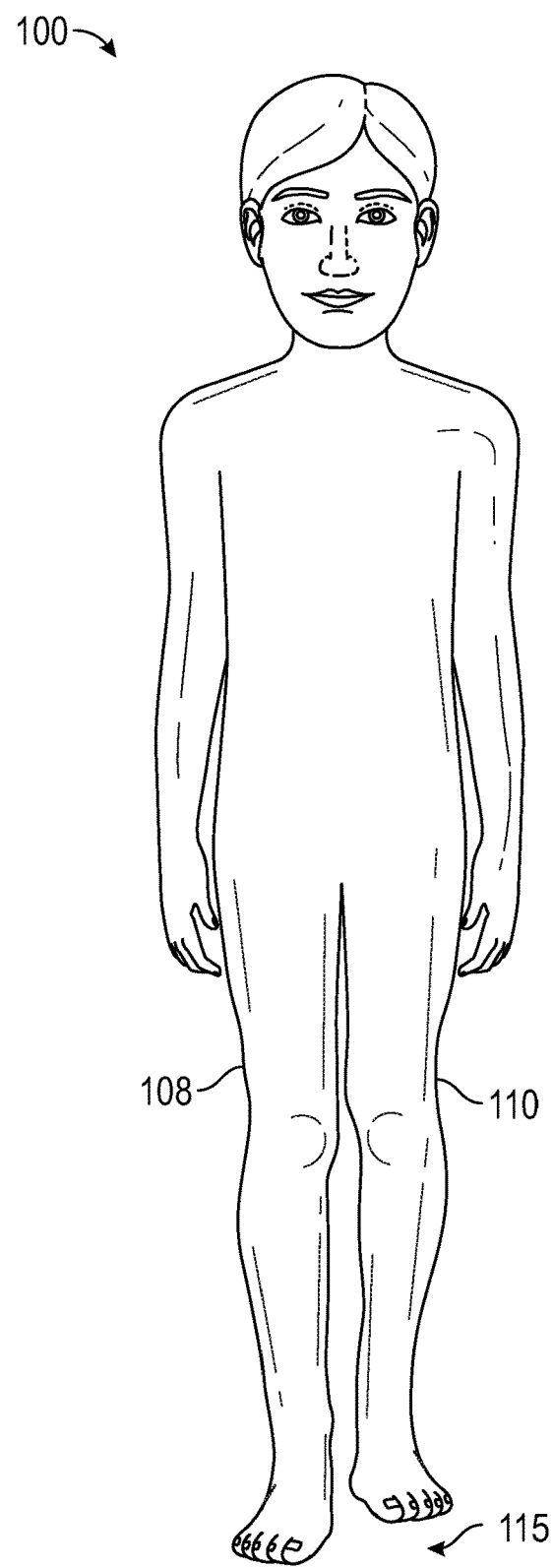
FIG. 1 is a front view of an illustrative person having leg length discrepancy (LLD).

Various aspects and examples of systems and methods relating to footwear to correct LLD are described below and illustrated in the associated drawings. Unless otherwise specified, a system for providing corrective footwear for LLD in accordance with the present teachings, and/or its various components may, but are not required to, contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

This Detailed Description includes the following sections, which follow immediately below: (1) Definitions; (2) Overview; (3) Examples, Components, and Alternatives; (4) Illustrative Combinations and Additional Examples; (5) Advantages, Features, and Benefits; and (6) Conclusion. The Examples, Components, and Alternatives section is further divided into subsections A through G, each of which is labeled accordingly.

Definitions

The following definitions apply herein, unless otherwise indicated.

"Substantially" means to be more-or-less conforming to the dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

Overview

In general, a method of providing corrective footwear for correcting leg length discrepancy (LLD) in accordance with aspects of the present teachings includes providing a left shoe having a first sole thickness and a right shoe having a second sole thickness that differs from the first sole thickness by the amount of LLD to be corrected. Footwear provided according to the present teachings may be pre-manufactured to accommodate various amounts of LLD, and therefore does not require lifts or deconstruction of existing footwear. Furthermore, footwear provided according to the present teachings can include open-toed footwear such as sandals or flip-flops having predetermined LLD corrections, whereas open-toed footwear generally cannot be corrected for LLD using prior art solutions such as lifts.

More specifically, the present methods typically include obtaining a plurality of pairs of shoes wherein the left and right shoes of each pair have the same sole thickness, and the plurality of pairs includes pairs having sole thicknesses spanning a predetermined range of thicknesses. A left shoe from a first pair and a right shoe from a second pair are selected to form a corrective pair of shoes wherein the difference between the thickness of the left shoe's sole and the thickness of the right shoe's sole is substantially equal to the amount of LLD to be corrected.

For example, a provider of corrective footwear may manufacture (or have manufactured) a plurality of pairs of shoes described above, wherein the left and right shoes of each pair have a same sole thickness, but wherein the plurality includes pairs having a variety of sole thicknesses. The provider may receive an order (e.g., from an individual consumer) for a pair of corrective footwear configured to correct a specified amount of LLD (e.g., 10 millimeters). Accordingly, the provider may select a left shoe from a first pair of the plurality of pairs and a right shoe from a second pair of the plurality of pairs, wherein the sole thicknesses of the selected left and right shoes differ by the specified amount of LLD. This method enables the shoe provider to offer corrective pairs of shoes suitable for treating a broad range of amounts of LLD by mass-producing pairs of right and left shoes, wherein the left and right shoes of a pair have the same sole thickness. Accordingly, corrective footwear according to the present teachings need not be specially manufactured and need not involve lifts or deconstruction/reconstruction of existing factory-made footwear.

Examples, Components, and Alternatives

The following sections describe selected aspects of exemplary corrective footwear for treating LLD, as well as related systems and/or methods. The examples in these sections are intended for illustration and should not be interpreted as limiting the entire scope of the present disclosure. Each section may include one or more distinct embodiments or examples, and/or contextual or related information, function, and/or structure.

A. Illustrative Corrective Footwear for LLD

Figure 2:
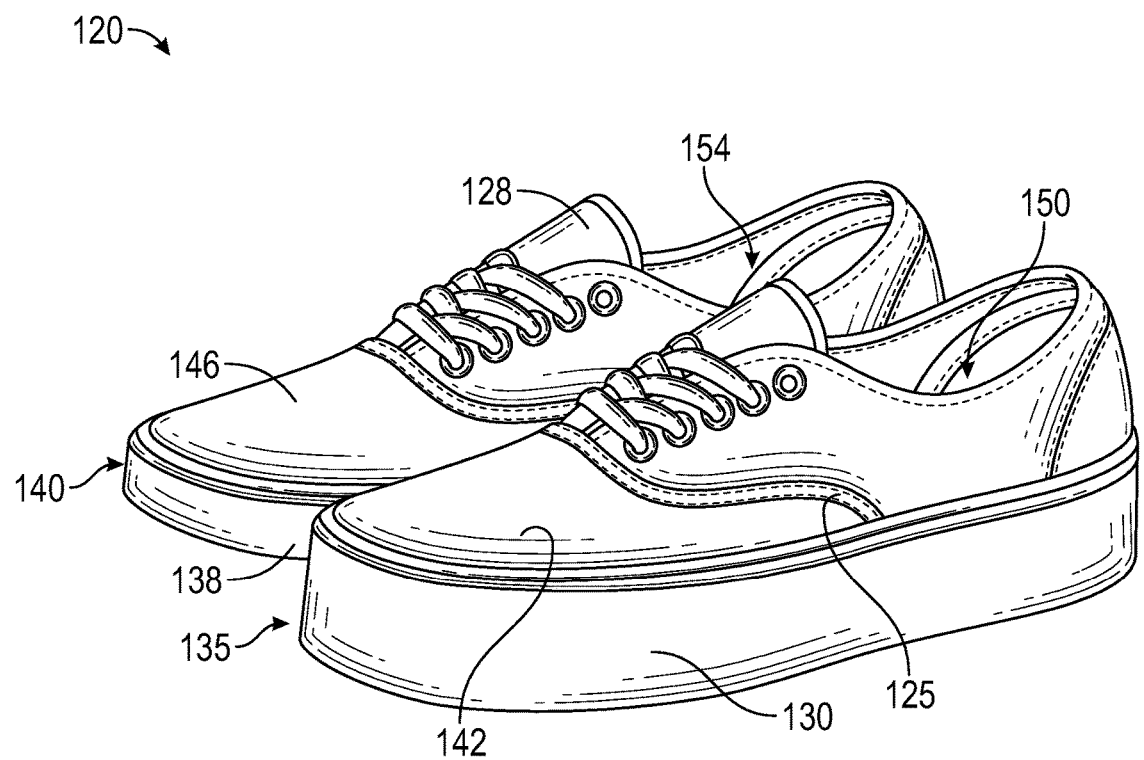
FIG. 2 is an isometric view of a pair of corrective footwear for LLD, in accordance with aspects of the present teachings.

With reference to FIGS. 1-2, this section describes an illustrative corrective footwear pair for correcting LLD, in accordance with aspects of the present teachings. The corrective footwear pair described in this section is an example of footwear designed to treat, correct, accommodate, and/or compensate for LLD, as described above.

FIG. 1 depicts a person 100 suffering from LLD. As FIG. 1 shows, person 100 has two legs of noticeably unequal length. The difference between the length of first leg 108 and the length of second leg 110 comprises an amount 115 of LLD. For example, person 100 may suffer structural LLD, functional LLD, and/or the like. As used herein, a nonzero amount 115 of LLD may refer to any amount of LLD other than zero that an individual seeks to correct (e.g., compensate for) by wearing suitable footwear. Illustrative nonzero amounts 115 may be less than one millimeter, between one millimeter and one inch, more than one inch, and/or any other suitable value.

FIG. 2 depicts an illustrative corrective pair of footwear 120, in accordance with aspects of the present teachings. Corrective pair 120 includes a left member 125 for wearing on a left foot and a right member 128 for wearing on a right foot. Left member 125 has a first sole 130 having a first sole thickness 135, and right member 128 has a second sole 138 having a second sole thickness 140. Soles 130, 138 may each comprise an insole, an outsole, a midsole, and/or any other suitable components. The difference between first sole thickness 135 and second sole thickness 140 typically corresponds to the amount of LLD corrective pair 120 is configured to correct. Accordingly, a person 100 having nonzero LLD amount 115 may compensate for their LLD by wearing a corrective pair of footwear having left and right members selected such that the difference between the first and second sole thicknesses is substantially equal to nonzero amount 115.

Left member 125 has a first upper 142, and right member 128 has a second upper 146. Uppers 142, 146 are connected to respective soles 130, 138 and are each configured to receive a wearer's foot. A first interior volume 150 is defined by first upper 142 and first sole 130, and a second interior volume 154 is defined by second upper 146 and second sole 138. First and second interior volumes 150, 154 generally define the amount of space available for a foot on which the respective member 125, 128 is worn. Typically, first interior volume 150 of left member 125 is substantially identical to second interior volume 154 of right member 128, even though first sole 130 and second sole 138 have different thicknesses.

In the example depicted in FIG. 2, soles 130, 138 each have substantially uniform thicknesses throughout each sole. In other examples, however, the sole thickness may be nonuniform. For example, in some cases, the sole of one or both shoes may be thicker at the heel than at the toe (e.g., in a wedge-type shoe). As another example, the sole may be contoured to support the wearer's foot. In general, first sole thickness 135 and second sole thickness 140 may be defined at any position of the respective shoe suitable for characterizing the amount of LLD correctible by corrective pair 120. For example, the sole thickness may be defined as the distance between an uppermost part of the sole (e.g., a top of an insole) and a bottommost part of the sole (e.g., a bottom of an outsole) at the portion of the sole located underneath the ball and/or heel of a wearer's foot.

Left member 125 and right member 128 may comprise any type of shoe suitable for manufacturing in accordance with the present teachings. Illustrative types of shoe may include, without limitation, sneakers, boots, specialized athletic shoes, sandals, flip flops, pumps, and/or flat shoes. Notably, suitable shoe types may include open-toed shoes, open-heeled shoes, and any other shoes wherein the shoe upper covers a relatively small portion of the wearer's foot and/or wherein the shoe includes at least one opening between the upper and the sole. For example, left member 125 and right member 128 may comprise flip flops, sandals, mules, slides, slingbacks, clogs, d'Orsay shoes, huaraches, and/or the like. In contrast, known devices for treating LLD, such as shoe inserts or lifts, require that the upper contact the sole at substantially all of the perimeter of the sole, so that the upper can retain the insert or lift within the shoe.

B. Illustrative Pluralities of Pairs of Footwear

With reference to FIGS. 3-5, this section describes illustrative pluralities of pairs of footwear for use in conjunction with methods for treating LLD, in accordance with aspects of the present teachings.

FIG. 3 depicts a first plurality 200 of pairs 202 of footwear. Each pair 202 includes a left member 204 having a left sole 205, and a right member 206 have a right sole 207. Left member 204 and right member 206 of each pair 202 have an identical first sole thickness; in other words, a thickness of left sole 205 is identical to a thickness of right sole 207. Left member 204 and right member 206 are simply a normal, mirror-image pair of footwear 202.

In some examples, soles 205 each comprise first and second layers 210, 211, and soles 207 each comprise first and second layers 214, 215. Generally, left member 204 and right member 206 are each manufactured such that the first and second layers are integral to the respective sole; that is, the first and second layers are manufactured as part of the sole rather than added to the sole after manufacture.

FIG. 4 depicts a second plurality 220 of pairs 222 of footwear. Like pairs 202 of first plurality 200, each pair 222 of second plurality 220 includes a left member 224 having a left sole 225, and a right member 226 having a right sole 227. Left member 224 and right member 226 of each pair 222 have an identical second sole thickness that is different from the first sole thickness. Thus, left member 224 and right member 226 for another normal, mirror-image pair of footwear 222, but with a different sole thickness than the sole thickness of the pair of footwear 202 formed by left and right members 204, 206.

In some examples, soles 225 each comprise first and second layers 230, 231, and soles 227 each comprise first and second layers 234, 235. In some cases, first layer 230 of left member 224 and first layer 210 of left member 204 have substantially identical thicknesses, and first layer 234 of right member 226 and first layer 214 of right member 206 have substantially identical thicknesses. In contrast, second layer 231 of left member 224 and second layer 211 of left member 204 have different thicknesses, and second layer 235 of right member 226 and second layer 215 of right member 206 have different thicknesses. In other words, there may be little or no difference between the first sole layers of first plurality 200 and second plurality 220, such that the sole thicknesses of members of first plurality 200 differ from the sole thicknesses of members of second plurality 220 because the second sole layers have different thicknesses. The consistency of the first sole layers between pluralities of pairs of footwear may simplify tooling and/or other aspects of manufacturing the footwear. This may be a particular advantage in cases wherein uppers of the footwear are directly connected to the first sole layer rather than to the second sole layer.

In the example depicted in FIGS. 3-4, the footwear of pairs 202 and 222 comprise open-toed sandals or flip flops. However, pairs 202 and 222 may comprise any suitable type of footwear (e.g., as described above with reference to corrective pair 120). Typically, the footwear of pairs 202 and 222 comprise the same style of footwear. For example, left member 204 and left member 224 may have identically shaped uppers, and right member 206 and right member 226 may have identically shaped uppers. Furthermore, left member 204 and left member 224 typically have an identical first interior volume, and right member 206 and right member 226 typically have an identical second interior volume.

As shown in FIG. 5, a pair of corrective footwear 240 may be formed by selecting one of the left members 204 from first plurality 200 and one of the right members 226 from second plurality 220. Alternatively, a pair of corrective footwear may be formed by selecting one of the right members 206 from first plurality 200 and one of the left members 224 from second plurality 220. In either case, the corrective footwear pair includes two members having different sole thicknesses, and is therefore suitable for treating a person having a nonzero LLD amount equal to the difference in the sole thicknesses.

Each pair of footwear of first and second pluralities 200 and 220 may be manufactured according to any suitable method using any suitable equipment, including standard methods and/or equipment not specifically dedicated to manufacturing LLD-corrective footwear. In some examples, manufacturing the pairs of footwear includes forming at least a portion of each footwear member using a mold. For example, the soles of the footwear may be formed in a mold.

Although FIGS. 3-5 depict two pluralities 200 and 220, additional pluralities of pairs of footwear may be also be provided. For example, there may also be a third plurality of footwear pairs having left and right members that share a third sole thickness different from the first and second thicknesses. By selecting footwear members from the first and second, first and third, or second and third pluralities of pairs, it is possible to form a corrective pair configured to treat any one of three different amounts of LLD; namely, LLD amounts equal to the difference between the first and second sole thicknesses, the first and third sole thicknesses, and the second and third sole thicknesses. Furthermore, for each of the three amounts of LLD to be treated, it is possible to form a corrective footwear pair wherein the left member is thicker than the right member or wherein the left member is thinner than the right member. Any suitable number of pluralities of footwear pairs may be provided, resulting in any desired amount of possible LLD correction.

C. Illustrative Order for Corrective Footwear

Figure 6:
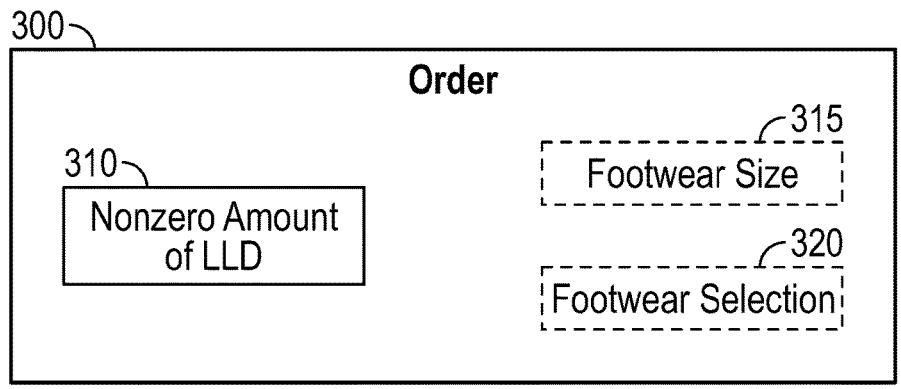
FIG. 6 is a schematic diagram of an illustrative order for corrective footwear, in accordance with aspects of the present teachings.

With reference to FIG. 6, this section describes an illustrative order 300 for a pair of corrective footwear for treating LLD, such as an order that might be placed by a consumer, in accordance with aspects of the present teachings.

Order 300 comprises a request for one or more pairs of corrective footwear for treating LLD. For example, a retailer selling corrective footwear may receive order 300 from a person who suffers from LLD and wants to purchase a pair of corrective footwear to treat their LLD, or from a third party wishing to purchase corrective footwear for an LLD sufferer. In some examples, order 300 is an electronic order created using a user interface of a data processing system such as a computer or mobile device. For example, order 300 may be created by a consumer accessing a retail website via a web browser and/or mobile application. Alternatively, or additionally, order 300 may be created on a data processing system at a retail store, office, and/or other suitable location, and may be created by a consumer and/or by a store employee assisting the consumer. In other examples, order 300 may be created by a consumer filling out a printed form (e.g., on paper), providing information to a retailer in person and/or via telephone, and/or by any other suitable means by which a consumer places an order for goods to be purchased.

As shown schematically in FIG. 6, order 300 includes an indication 310 of a nonzero amount of LLD to be corrected by the pair of corrective footwear being ordered. In some examples, indication 310 includes an exact or nearly exact amount of LLD suffered by the person who is to wear the corrective footwear. Alternatively, or additionally, indication 310 may indicate an LLD amount that is rounded (e.g., rounded to a nearest millimeter or fraction of a millimeter, and/or in any other suitable manner).

Typically, indication 310 further includes an indication of which one of the person's legs is shorter and/or which one is longer, so that appropriate left and right members may be included in the corrective footwear pair being ordered. For example, if the person suffers LLD such that their left leg is shorter than their right leg, then footwear suitable to treat their LLD should include a left member having a thicker sole and a right member having a thinner sole.

Order 300 may further include footwear size indication 315 relating to the person's shoe size and/or width. For example, footwear size indication 315 may include a numerical shoe size and a request for a narrow, medium, or wide sole. Order 300 may further include a footwear selection 320 identifying a model, style, and/or color of footwear to be ordered. Footwear size indication 315 and footwear selection 320 are typically similar to components of an order for a standard pair of non-corrective footwear.

D. Illustrative Method of Providing Open-Toed Sandals to Correct Leg Length Discrepancy This section describes steps of an illustrative method 400 for providing open-toed sandals to correct leg length discrepancy; see FIG. 7. Aspects of corrective footwear pairs described above may be utilized in the method steps described below. Where appropriate, reference may be made to components and systems that may be used in carrying out each step. These references are for illustration, and are not intended to limit the possible ways of carrying out any particular step of the method.

Figure 7:
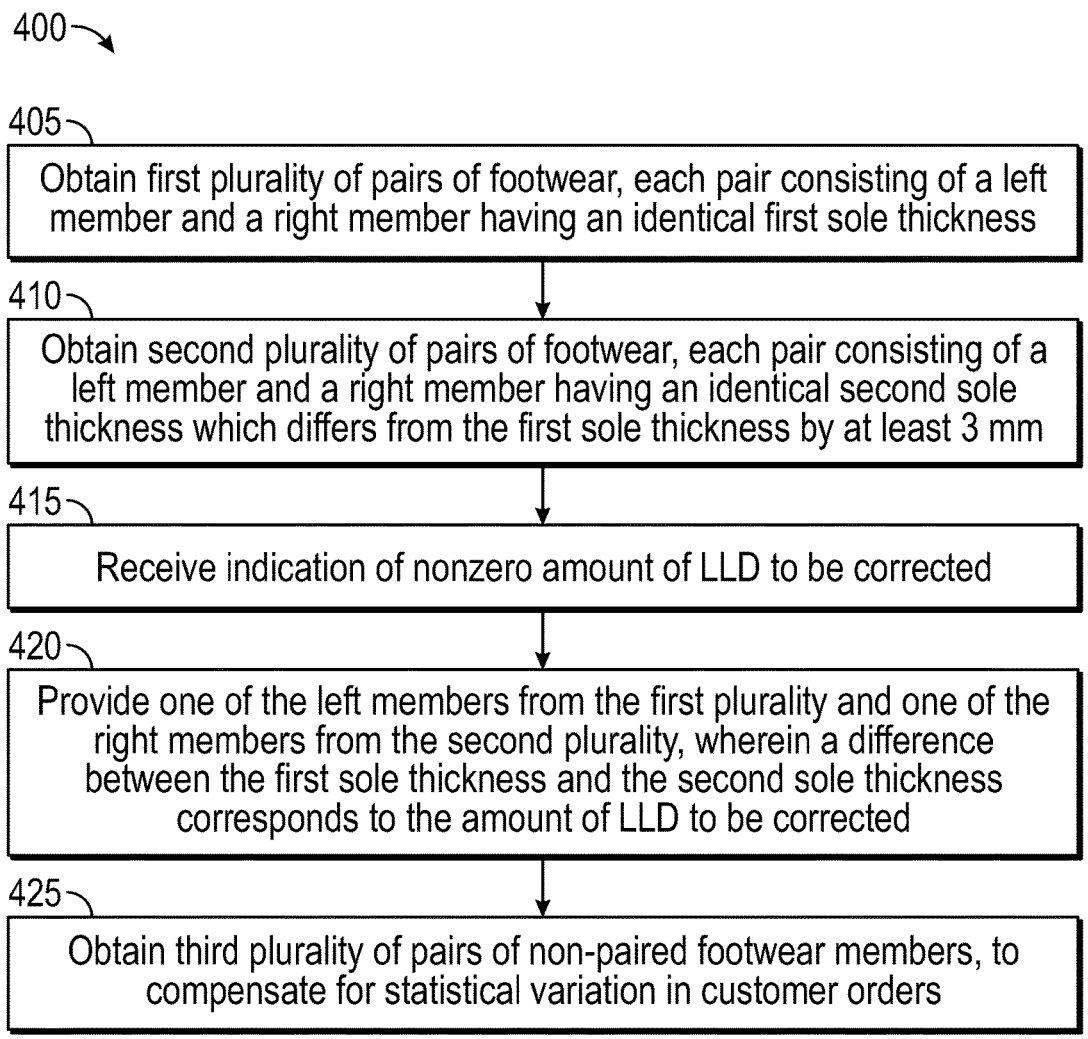
FIG. 7 is a flow chart depicting steps of an illustrative method of providing open-toed sandals to correct LLD according to aspects of the present teachings.

FIG. 7 is a flowchart illustrating steps performed in an illustrative method, and may not recite the complete process or all steps of the method. Although various steps of method 400 are described below and depicted in FIG. 7, the steps need not necessarily all be performed, and in some cases may be performed simultaneously or in a different order than the order shown.

At step 405, method 400 includes obtaining a first plurality of pairs of sandals. Each pair of the first plurality consists of a left member (e.g., a sandal configured to be worn on a left foot) and a right member (e.g., a sandal configured to be worn on a right foot) having an identical first sole thickness.

At step 410, method 400 includes obtaining a second plurality of pairs of sandals. Each pair of the second plurality consists of a left member and a right member having an identical second sole thickness. The second sole thickness differs from the first sole thickness by at least 3 millimeters (mm), and may differ by as much as 1 inch or more.

The sandals of the first and second pluralities of pairs of sandals are open-toed (e.g., having an upper configured to expose at least a significant portion of the wearer's toes), and may also be open-heeled (e.g., having an upper configured to expose at least a significant portion of the wearer's heel). The sandals of the first and second pluralities may comprise shoes unsuitable for accommodating lifts or inserts used in known systems from treating LLD. Obtaining the sandals of the first and second pluralities may include manufacturing the sandals, having the sandals manufactured, purchasing the sandals, and/or taking any other suitable steps.

At step 415, method 400 includes receiving an indication of a nonzero amount of LLD to be corrected. The difference between the first sole thickness and the second sole thickness corresponds to the amount of LLD to be corrected. For example, the difference may be substantially equal to the amount of LLD to be corrected, and/or may be within a predetermined tolerance of the amount of LLD to be corrected. The indication of the nonzero amount of LLD to be corrected may include an indication as to whether the LLD includes a left leg shorter than a right leg or a right leg shorter than a left leg.

At step 420, method 400 includes providing one of the left members from the first plurality and one of the right members from the second plurality. Because the difference between the first and second sole thicknesses corresponds to the amount of LLD to be corrected, the left and right members provided at step 420 form a pair of sandals suitable for correcting the indicated amount of LLD. If the LLD to be corrected includes a left leg shorter than a right leg, then the sole thickness of the left member (e.g., the first sole thickness) is greater than the sole thickness of the right member (e.g., the second sole thickness). If, on the other hand, the LLD to be corrected includes a left leg longer than a right leg, then the sole thickness of the left member is less than the sole thickness of the right member.

In some cases, method 400 also may include, at step 425, obtaining at least a third plurality of non-paired footwear members, to compensate for statistical variation in customer orders. For instance, if customers place orders requiring a greater number of left footwear members having a particular sole thickness than right footwear members having that same sole thickness, method 400 could include obtaining addition left footwear members having the desired thickness. This can avoid building up a surplus of footwear of any particular thickness or orientation (i.e., left-footed or right-footed).

E. Illustrative Method of Treating Leg Length Discrepancy without the Use of an Insertable Footwear Lift This section describes steps of an illustrative method 500 for treating leg length discrepancy without the use of an insertable footwear lift; see FIG. 8. Aspects of corrective footwear pairs described above may be utilized in the method steps described below. Where appropriate, reference may be made to components and systems that may be used in carrying out each step. These references are for illustration, and are not intended to limit the possible ways of carrying out any particular step of the method.

Figure 8:
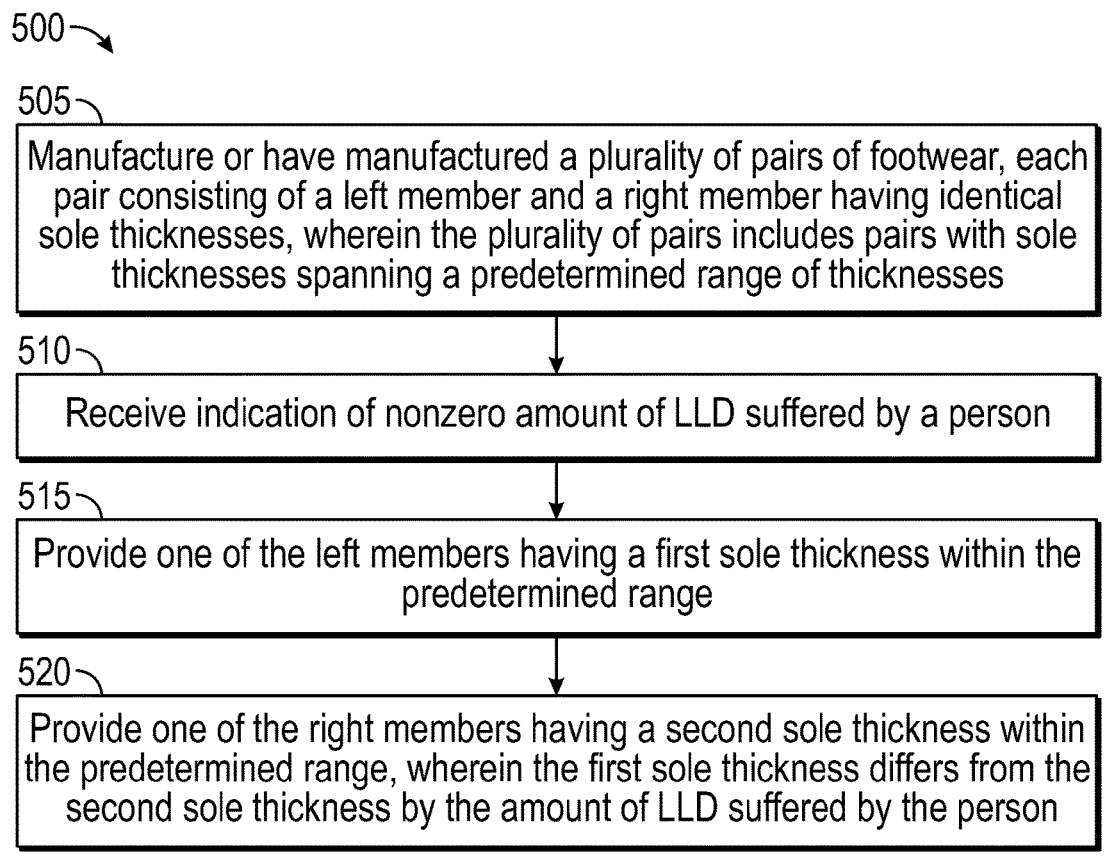
FIG. 8 is a flow chart depicting steps of an illustrative method of treating LLD without the use of an insertable footwear lift according to aspects of the present teachings.

FIG. 8 is a flowchart illustrating steps performed in an illustrative method, and may not recite the complete process or all steps of the method. Although various steps of method 500 are described below and depicted in FIG. 8, the steps need not necessarily all be performed, and in some cases may be performed simultaneously or in a different order than the order shown.

At step 505, method 500 includes manufacturing or having manufactured a plurality of pairs of footwear. Each pair of footwear consists of a left member and a right member having identical sole thicknesses. The plurality of pairs includes pairs with sole thicknesses spanning a predetermined range of thicknesses.

As described below, a left member and a right member having different sole thicknesses (e.g., from different pairs) may be selected to form a pair of corrective footwear for treating LLD. Accordingly, the predetermined range of thicknesses is generally designed to enable the selection of left and right members to treat a range of amounts of LLD. Generally, the difference between the greatest and the smallest thicknesses in the range corresponds to the largest amount of LLD treatable by footwear selected appropriately from the plurality of pairs. For example, if the difference between the thickest and thinnest thicknesses in the range is 1 inch, then the greatest amount of LLD treatable is approximately 1 inch. The smallest amount of LLD treatable is generally determined by the smallest difference in thickness between pairs of thicknesses in the range. For example, if the closest two non-identical thicknesses in the range of thicknesses spanned by pairs in the plurality differ by 3 mm, then the smallest amount of LLD treatable is approximately 3 mm.

At step 510, method 500 includes receiving an indication of a nonzero amount of LLD suffered by a person. For example, the person may be a consumer wishing to purchase a pair of corrective footwear for treating their LLD. The nonzero amount of LLD may be between 1 mm and 2 inches, between 3 mm and 1 inch, and/or within any other range suitable for treating LLD in accordance with aspects of the present teachings.

At step 515, method 500 includes providing one of the left members having a first sole thickness. At step 520, method 500 includes providing one of the right members having a second sole thickness. The first and second sole thicknesses are within the predetermined range of thicknesses spanned by the plurality of pairs. The first sole thickness differs from the second sole thickness by the amount of LLD suffered by the person (e.g., by the amount indicated in the indication received at step 510). Accordingly, the left member and the right member provided at steps 515 and 520 form a pair of corrective footwear configured to treat and/or compensate for the amount of LLD suffered by the person. The corrective footwear pair enables the person's LLD to be treated without the use of an insertable footwear lift. Accordingly, the footwear of the plurality of footwear described above with reference to step 505 may comprise styles of footwear unsuitable for use with an insertable lift.

F. Illustrative Method of Providing Footwear to Correct Leg Length Discrepancy

Figure 9:
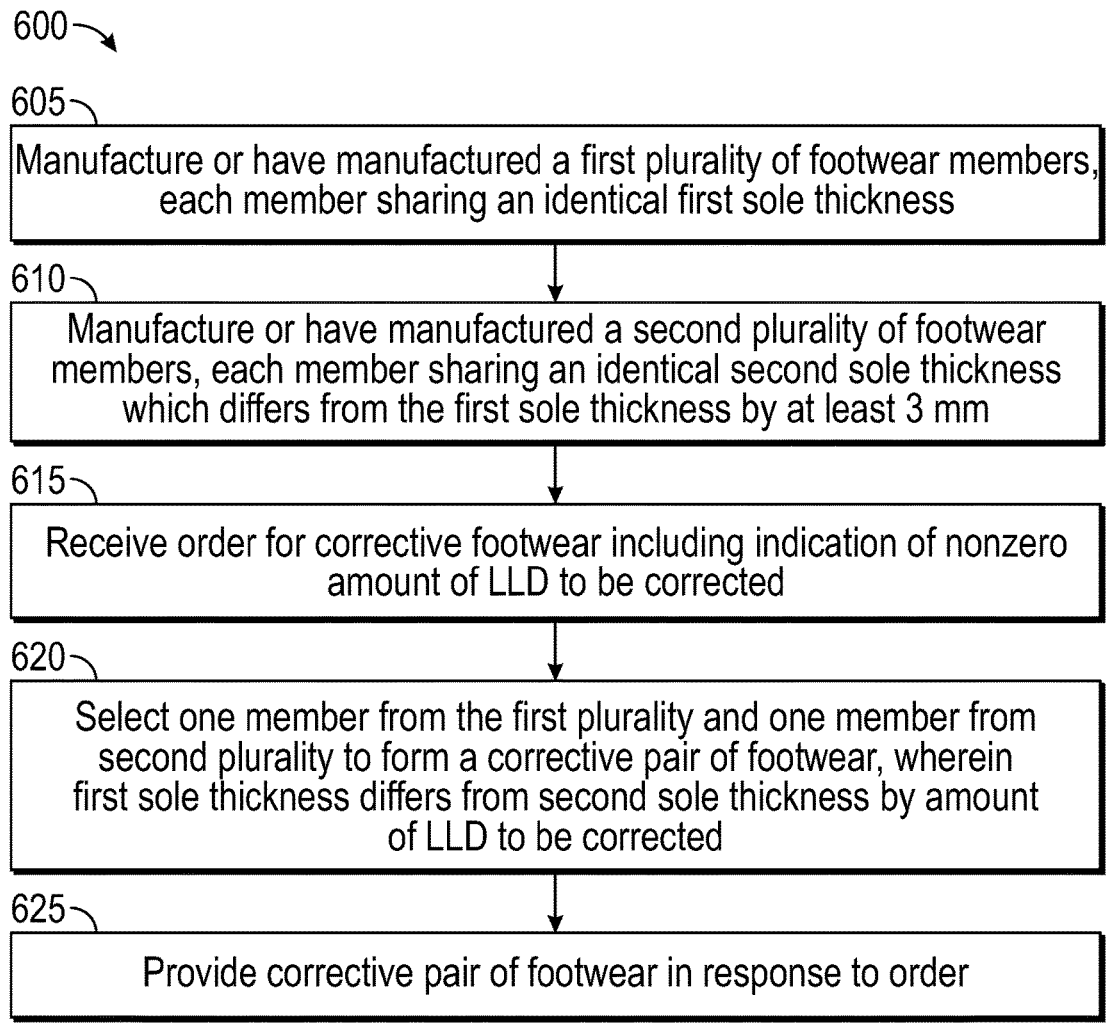
FIG. 9 is a flow chart depicting steps of an illustrative method of providing footwear to correct LLD according to aspects of the present teachings.

This section describes steps of an illustrative method 600 for providing footwear to correct leg length discrepancy; see FIG. 9. Aspects of corrective footwear pairs described above may be utilized in the method steps described below. Where appropriate, reference may be made to components and systems that may be used in carrying out each step. These references are for illustration, and are not intended to limit the possible ways of carrying out any particular step of the method.

FIG. 9 is a flowchart illustrating steps performed in an illustrative method, and may not recite the complete process or all steps of the method. Although various steps of method 600 are described below and depicted in FIG. 9, the steps need not necessarily all be performed, and in some cases may be performed simultaneously or in a different order than the order shown.

At step 605, method 600 includes manufacturing or having manufactured a first plurality of footwear members. Each member of the first plurality shares an identical first sole thickness. The members of the first plurality may all be left-footed members or right-footed members, or may include both left-footed and right-footed members in equal or unequal numbers.

At step 610, method 600 includes manufacturing or having manufactured a second plurality of footwear members. Each member of the second plurality shares an identical second sole thickness. The second sole thickness differs from the first sole thickness by a nonzero amount, such as at least 3 mm. The members of the second plurality may all be left-footed members or right-footed members, or may include both left-footed and right-footed members in equal or unequal numbers.

At step 615, method 600 includes receiving an order for corrective footwear including an indication of a nonzero amount of LLD to be corrected. In some examples, the order comprises an electronic order received via a computer network such as the Internet. Alternatively, or additionally, the order may be received via a postal service, telephone, in-person interaction, and/or by any other suitable method. Typically, the received order is substantially similar to a typical order for a pair of ordinary non-corrective footwear, except in that the order received at step 615 includes an indication of a nonzero amount of LLD to be corrected. The order may be received by a salesperson in a retail store that stocks a supply of footwear having different sole thicknesses.

At step 620, method 600 includes selecting one of the members from the first plurality and one of the members from the second plurality to form a corrective pair of footwear. The first sole thickness differs from the second sole thickness by the amount of LLD to be corrected.

At step 625, method 600 includes providing the corrective pair of footwear in response to the order. For example, the corrective pair of footwear may be sold to a consumer who placed the order.

G. Illustrative Combinations and Additional Examples

This section describes additional aspects and features of corrective footwear and related methods for treating LLD, presented without limitation as a series of paragraphs, some or all of which may be alphanumerically designated for clarity and efficiency. Each of these paragraphs can be combined with one or more other paragraphs, and/or with disclosure from elsewhere in this application, in any suitable manner. Some of the paragraphs below expressly refer to and further limit other paragraphs, providing without limitation examples of some of the suitable combinations.

A. A method of providing open-toed sandals to correct leg length discrepancy, comprising obtaining a first plurality of pairs of sandals, each pair of the first plurality consisting of a left member and a right member having an identical first sole thickness; obtaining a second plurality of pairs of sandals, each pair of the second plurality consisting of a left member and a right member having an identical second sole thickness which differs from the first sole thickness by at least 3 millimeters; receiving an indication of a nonzero amount of leg length discrepancy to be corrected; and providing one of the left members from the first plurality and one of the right members from the second plurality; wherein a difference between the first sole thickness and the second sole thickness corresponds to the amount of leg length discrepancy to be corrected.

A1. The method of paragraph A, wherein all of the left members have an identical first interior volume, and all of the right members have an identical second interior volume.

A2. The method of any one of paragraphs A through A1, wherein the left members of the first plurality and the left members of the second plurality each have respective uppers having an identical first shape, and the right members of the first plurality and the right members of the second plurality each have respective uppers having an identical second shape.

A3. The method of any one of paragraphs A through A2, wherein a respective sole of each of the left and right members comprises a first sole layer and a second sole layer, and all of the left members and all of the right members have an identical first sole layer thickness.

A4. The method of any one of paragraphs A through A3, wherein obtaining the first and second pluralities of pairs of sandals includes molding respective soles for each of the left members and each of the right members.

B. A method of treating leg length discrepancy without the use of an insertable footwear lift, comprising manufacturing or having manufactured a plurality of pairs of footwear, wherein each pair of footwear consists of a left member and a right member having identical sole thicknesses, and wherein the plurality of pairs includes pairs with sole thicknesses spanning a predetermined range of thicknesses; receiving an indication of a nonzero amount of leg length discrepancy suffered by a person; providing one of the left members having a first sole thickness within the predetermined range; and providing one of the right members having a second sole thickness within the predetermined range; wherein the first sole thickness differs from the second sole thickness by the amount of leg length discrepancy suffered by the person.

B1. The method of paragraph B, wherein the predetermined range of thicknesses spans at least one inch.

B2. The method of any one of paragraphs B through B1, wherein the predetermined range of thicknesses includes a thickness of 3 millimeters and a thickness of 24 millimeters.

B3. The method of any one of paragraphs B through B2, wherein the plurality of pairs includes pairs with at least eight different respective sole thicknesses.

B4. The method of any one of paragraphs B through B3, wherein the predetermined range of thicknesses includes a first thickness differing from a second thickness by no more than 3 millimeters.

B5. The method of any one of paragraphs B through B4, wherein all of the left members and all of the right members include at least one respective opening between an upper of the respective member and a sole of the respective member.

B6. The method of any one of paragraphs B through B5, wherein all of the left members and all of the right members comprise sandals.

B7. The method of any one of paragraphs B through B6, wherein all of the left members have an identical first interior volume, and all of the right members have an identical second interior volume.

B8. The method of any one of paragraphs B through B7, wherein manufacturing the plurality of pairs of footwear includes molding at least a portion of each member.

C. A method of providing footwear to correct leg length discrepancy, comprising manufacturing or having manufactured a first plurality of pairs of footwear, each pair of the first plurality consisting of a left member and a right member, wherein all the left members and all the right members of the first plurality share an identical first sole thickness; manufacturing or having manufactured a second plurality of pairs of footwear, each pair of the second plurality consisting of a left member and a right member, wherein all the left members and all the right members of the second plurality share an identical second sole thickness which differs from the first sole thickness by at least 3 millimeters; receiving an order for corrective footwear including an indication of a nonzero amount of leg length discrepancy to be corrected; selecting one of the left members from the first plurality and one of the right members from the second plurality to form a corrective pair of footwear, wherein the first sole thickness differs from the second sole thickness by the amount of leg length discrepancy to be corrected; and providing the corrective pair of footwear in response to the order.

C1. The method of paragraph C, wherein the order comprises an electronic order.

C2. The method of any one of paragraphs C through C1, wherein all of the left members and all of the right members include at least one respective opening between an upper of the respective member and a sole of the respective member.

C3. The method of any one of paragraphs C through C2, wherein all of the left members and all of the right members are open-toed.

C4. The method of any one of paragraphs C through C3, wherein all of the left members of the first and second pluralities of pairs have respective upper portions having an identical first shape, and all of the right members of the first and second pluralities of pairs have respective upper portions having an identical second shape.

C5. The method of any one of paragraphs C through C4, wherein manufacturing the plurality of pairs of footwear includes molding at least a portion of each member.

Advantages, Features, and Benefits

The different embodiments and examples of the LLD treatment devices and methods described herein provide several advantages over known solutions for treating LLD. For example, illustrative embodiments and examples described herein allow for LLD treatment without the use of insertable shoe lifts. Insertable shoe lifts occupy space within a shoe and therefore prevent the shoe from fitting the foot as intended, leading to discomfort, inadequate foot support, and excessive wear on the shoe. Accordingly, systems and methods described herein allow LLD to be treated without these problems.

Additionally, and among other benefits, illustrative embodiments and examples described herein allow for corrective footwear for treating LLD comprising footwear styles unsuitable for use with an insertable shoe lift, such as sandals.

Additionally, and among other benefits, illustrative embodiments and examples described herein allow corrective footwear for LLD to be mass-produced rather than custom-made or custom-modified. For example, as described herein, methods of providing corrective footwear may include obtaining pairs of shoes wherein the left and right members of each pair have an identical sole thickness. These pairs of shoes may be mass-produced. In contrast, known methods for providing LLD-corrective footwear typically include manufacturing pairs of shoes having different thicknesses, or modifying existing pairs of shoes to have different thicknesses, which is costly and potentially time-consuming.

Additionally, and among other benefits, illustrative embodiments and examples described herein allow a person having a nonzero amount of LLD to easily obtain a pair of corrective footwear suitable for treating that amount of LLD. In accordance with aspects of the present teachings, a person having LLD may place an order for corrective footwear simply by specifying their standard shoe size and the amount of LLD to be corrected. In contrast, known methods require a person with LLD to have one or more shoes custom-built or modified by a specialist (e.g., at an orthopedic shoe store). This is expensive and potentially inconvenient (e.g., if there are no suitable specialists nearby).

No known system or device can perform these functions. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

What is claimed is:

1. A method of providing open-toed sandals to correct leg length discrepancy, comprising:
   obtaining a first plurality of pairs of sandals, each pair of the first plurality consisting of a left member and a right member having soles with an identical first sole thickness, in which all layers of each of the soles are structurally integral to each respective sole;
   obtaining a second plurality of pairs of sandals, each pair of the second plurality consisting of a left member and a right member having soles with an identical second sole thickness which differs from the first sole thickness by at least 3 millimeters, in which all layers of each of the soles are structurally integral to each respective sole;
   receiving an indication of a nonzero amount of leg length discrepancy to be corrected;
   providing one of the left members from the first plurality and one of the right members from the second plurality;
   wherein a difference between the first sole thickness and the second sole thickness corresponds to the amount of leg length discrepancy to be corrected;
   wherein the members of the first plurality of sandals and the members of the second plurality of sandals all share a common style and an identical interior volume.

2. The method of claim 1, wherein the left members of the first plurality and the left members of the second plurality each have respective uppers having an identical first shape, and the right members of the first plurality and the right members of the second plurality each have respective uppers having an identical second shape.

3. The method of claim 1, wherein a respective sole of each of the left and right members comprises a first sole layer having an identical, common first thickness.

4. The method of claim 1, further comprising obtaining a third plurality of non-paired footwear members, to compensate for statistical variation in customer orders.

5. A method of providing footwear to correct leg length discrepancy, comprising:
   having manufactured a first plurality of footwear members having soles, each of the first plurality sharing an identical first sole thickness, in which all layers of each of the soles of the first plurality of footwear members are structurally integral to each respective sole;
   having manufactured a second plurality of footwear members having soles, each of the second plurality sharing an identical second sole thickness which differs from the first sole thickness by at least 3 millimeters, in which all layers of each of the soles of the second plurality of footwear members are structurally integral to each respective sole;
   wherein all the left members of the first and second pluralities of footwear members have upper portions that share a first identical shape, and all the right members of the first and second pluralities of footwear members have upper portions that share a second identical shape, which is a mirror image of the first identical shape;
   receiving an order for corrective footwear including an indication of a nonzero amount of leg length discrepancy to be corrected;
   selecting a first member from the first plurality of footwear members and a second member from the second plurality of footwear members to form a corrective pair of footwear, wherein the first sole thickness differs from the second sole thickness by the amount of leg length discrepancy to be corrected; and providing the corrective pair of footwear in response to the order.

6. The method of claim 5, wherein the order comprises an electronic order.

7. The method of claim 5, wherein all of the footwear members include at least one respective opening between an upper of the respective member and a sole of the respective member.

8. The method of claim 7, wherein all of the footwear members are open-toed.

9. The method of claim 5, wherein having manufactured the plurality of footwear members includes having molded at least a portion of each footwear member.

* * * * *